United States Patent [19]

De Lima

[11] Patent Number: 5,080,786
[45] Date of Patent: Jan. 14, 1992

[54] BIOMASS DIGESTER

[76] Inventor: Daniel De Lima, Box 10128, S10055, Stockholm, Sweden

[21] Appl. No.: 363,182

[22] Filed: Jun. 5, 1989

Related U.S. Application Data

[63] Continuation-in-part of Ser. No. 933,933, Nov. 23, 1986, abandoned.

[51] Int. Cl.$^5$ .......................... C02F 11/14; C12M 1/00
[52] U.S. Cl. ..................................... 210/218; 210/219; 210/258; 210/539
[58] Field of Search ............... 210/603, 218, 219, 258, 210/170, 523, 539, 540

[56] References Cited

U.S. PATENT DOCUMENTS

| | | | |
|---|---|---|---|
| 3,933,628 | 1/1976 | Varani | 210/603 |
| 4,169,048 | 9/1979 | Albers, Sr. | 210/603 |
| 4,211,647 | 7/1980 | Friedman et al. | 210/603 |
| 4,323,367 | 4/1982 | Ghosh | 210/603 X |
| 4,334,997 | 6/1982 | Peterson | 210/603 |

FOREIGN PATENT DOCUMENTS

| | | |
|---|---|---|
| 1049415 | 12/1953 | France . |
| 1442390 | 5/1966 | France . |
| 1496006 | 8/1967 | France . |

Primary Examiner—Thomas Wyse

[57] ABSTRACT

An air-tight containment structure for the digestion of biomass may be collapsed under atmospheric pressure by drawing a vacuum therein, thereby compressing the contained fiber matrix and enhancing the wetting of the biomass. Reagents may be added in quantities to wet only an initial upper layer, and then dispersed downwardly into a further layer by addition of a displacing liquid.

5 Claims, 4 Drawing Sheets

BIOMASS DIGESTER

This application is a Continuation-In-Part application to application Ser. No. 06/933,933 filed Nov. 23, 1986, now abandoned.

FIELD OF INVENTION

This invention relates to a system for digesting cellulose-based materials in the form of biomass to produce improved animal feed and useful chemicals. More particularly it relates to a containment structure for enclosing and manipulating biomass during the digestion, drying and wetting process and for methods of utilizing that structure.

BACKGROUND TO THE INVENTION

Cellulose-based biomass may be hydrolyzed to sugars and the sugars may then be used for the production of yeasts. The yeasts can then be used as animal food stuffs or the sugars applied to produce useful chemicals such as ethanol and furfural.

According to one known process a weak acid solution is applied as reagent to the biomass to extract hemi-cellulose and improve the permeability of the cellulose. The hemi-cellulose may be further hydrolyzed to hexoses and pentoses. One of the costs in this, or any biomass digester system, is the amount of reagent solution employed.

Biomass is generally fibrous and of low density. It is necessary to contact the biomass with the activating solution in order to initiate the desired reaction. The high percentage of voids in biomass has previously required the use of large amounts of reagents to effect the desired reaction.

It is also known to apply a vacuum to material to be digested, prior to application of a reagent. This procedure has, however, been directed to de-aerating the digestible material itself so as to facilitate more through penetration of the reagent into the substance of the biomass itself. References to this type of procedure may be found in U.S. Pat. Nos. 4,057,461; 3,532,594; 3,278,367; 3,259,538; 3,076,501 and 2,694,632.

It is also known to effect a consolidation of silage through vacuum compression, as part of a process for effecting the anaerobic digestion of silige. c.f., "Effect on Intake and Production of Dairy Cows of Feeding Three High-Moisture Siliges Having Different Fermentation Characteristics" by R. J. Lancaster et al, 1974 New Zealand Journal of Experimental Agriculture, vol. 2, 389-92; and "High-Moisture Silage from Mixed Pasture Herbage as a Feed for Lactating Dairy Cows" by J. B. Hutton et al, New Zealand Journal of Agricultural Research (1971) vol. 14, 393-405; and "Quality Storage Losses of Silages Made in Bunkers, Stacks, and by Vacuum Compression" by R. J. Lancaster, New Zealand Journal of Agricultural Research (1968) vol. 11, p. 63-79. See also French patents 1,442,390 and 1,049,415.

The application of vacuum in the prior art has not been resorted to as a means for effecting compaction of the digestible biomass in conjunction with the application of reagents to thereby improve the wetting of the biomass and effect a reduction of the quantity of reagent required.

It is further known to agitate a liquid or slurry, such as sewage sludge in a digester, by periodically inflating and deflating a bladder immersed therein, c.f., U.K. patent 2,056,870 issued Mar. 25, 1981, for an invention by R. C. Baskerville et al. However, no use is known of the application of such a bladder to the agitation of a biomass matrix, in conjunction with the vacuum compaction and chemical treatment of such biomass with reagents. Further, special advantages may be obtained in choosing the location of such bladders.

The prior art also discloses in U.S. Pat. No. 4,176,203 a process for progressively distributing an alkaline liquid across the top surface of a mass of ligno-cellulosic material. This progressive distribution is achieved mechanically by moving the liquid distributing member reciprocally across the upper surface of the biomass. No attempt is made to control the downward displacement over time of the applied reagent, in progressive stages which proceed in conjuction with the exhaustion of the digestion process in consecutive layers of the biomass.

The present invention relates to a structure for containing biomass for digestion. More particularly it provides a means by which:

(1) biomass may be more effectively wetted (?) reduced quantities of reagents may be used to effect various stages of the digestion process, (3) valuable products may be recovered at the end of the process;

(4) biomass may be sterilized for long term storage; and (5) biomass may be sterilized and then exposed to preferred species of micr-organisms.

The latter aspects of the invention are useful in providing a means for controlling the yeast-reaction, and in some applications, arresting the decay of biomatter in the digester.

In many countries crops producing waste biomass are brought-in over a short period e.g. 1-3 months, during the year. Where such biomass may be converted to animal feed, storage becomes a problem. Animals need to consume feed continuously, 12 months a year. In the tropics it is particularly difficult to store biomass for long periods as head and moisture contribute to the rapid rotting of vegetable matter.

The biomass containment structure of the type specified herein can be used to store biomass for long periods of time, even in the tropics. Once sealed within the structure, the biomass may be sterilized with a strong acid. This "pickling" procedure is facilitated by the agitation that may be developed through vacuum compaction and release of the vacuum. When the containment structure is composed principally of plastic or hydrocarbon film or sheeting, large volumes of biomass so treated may be stored at reduced cost.

SUMMARY OF THE INVENTION

The containment structure of the invention used for biomass digestion is provided with a compressible, enveloping air-tight enclosure, having an upper cover, which may be in the form of a flexible sheet, which is adapted to be displaced downwardly into said structure under the influence of reduced internal air pressure. Within this enveloping enclosure may be placed fibrous, compressible biomass, with reagent-distribution and collection systems installed above and below the biomass. When it is desired to wet the biomass with reagent, the requisite reduced quantity of reagent is applied either from above, from where it may fall by gravity, or from below. A vacuum is then drawn within the enveloping enclosure allowing the atmospheric air pressure to compact the biomass and reduce the percentage of voids. This allows for the wetting of more biomass with a given quantity of reagent. Alternately, less reagent may be used to effect this wetting process.

The procedure of applying a vacuum may be repeated, with intervening relaxations of pressure, in order to agitate the biomass and further enhance the wetting of the contents of the containment structure.

Once the reagent has been infiltrated into the biomass matrix, the vacuum may be released and the reaction allowed to proceed on the basis that the reagent has been distributed with improved efficiency. Where useful gases are generated, they may be drawn off through a gas-extraction system. Where liquid products are produced they may be drawn off by gravity accumulation and removal through the collection system. This process may be enhanced by relaxing the vacuum and reapplying the pressure created by drawing a vacuum, thereby re-compressing the biomass, and assisting in the expression of the products of the reactions that have occurred.

By a further feature of the invention the floor of the containment structure may be provided with localized inflatable bladders. By inflating such bladders with gas or liquid the biomass matrix may be disturbed and agitated so as to enhance the efficiency of the digestion process. The bladders may be so placed between the inlets of the collection system as to direct the flow of fluids under gravity towards such inlets.

By a further feature of the invention, a limited quantity of reagent may be applied to the upper surface of the biomass, in a quantity insufficient to wet more than an upper layer, even with vacuum compression. Then the digestion process may be allowed to proceed in the wetted upper layer.

Subsequently, when the digestion process has been essentially exhausted in the upper layer, a displacing liquid may be applied from the upper distribution system. This liquid is so selected as to cause the residual reagent to be moved downward into a lower layer within the biomass, that has not been exhausted through digestion. Water can serve as a suitable liquid for this purpose, even allowing that it may partially enter into a solution with the reagent. This displacement process may again be facilitated by drawing and relaxing a vacuum within the enveloping enclosure so as to allow the atmospheric pressure to compress the fiber matrix and agitate the biomass.

This process of displacing the active reagent downward may be repeated through successive layers, thus effecting a wave of zone reactions over time.

By a further feature of the invention the acidity of the wetted biomass in its sealed enclosure may be adjusted to such a degree e.g. 3.0 pH, that the microbial activity therein is arrested. The biomass in the digester may then be stored in this "pickled" condition pending a future date when it is desired for the reaction to continue. Reactivation of certain yeast growth is effected through raising the pH.

These and other features of the invention will be apparent from the description of the preferred embodiment that follows hereafter.

DESCRIPTION OF THE PREFERRED EMBODIMENTS

Figure 1:
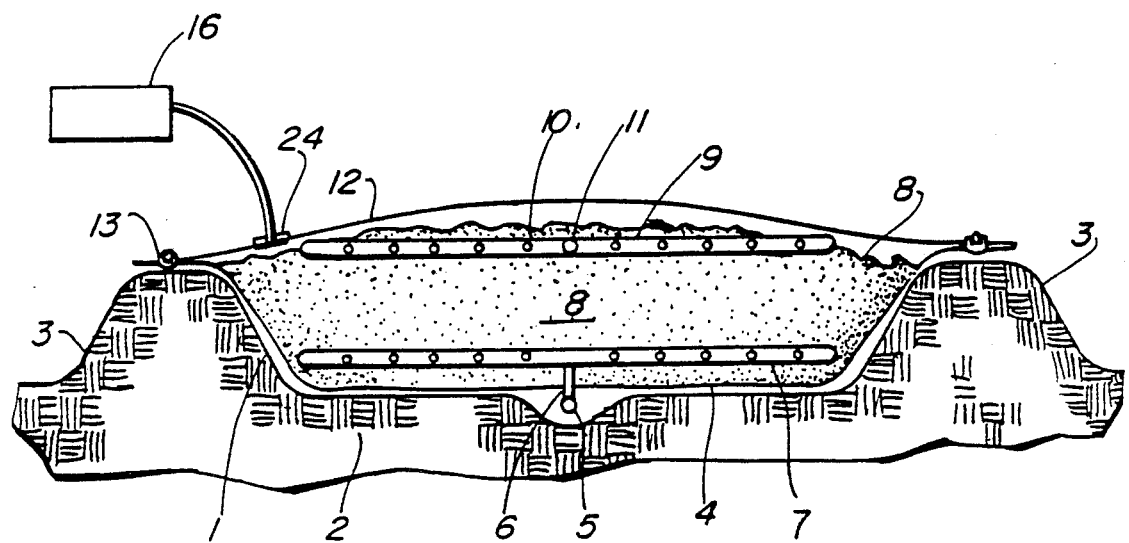
FIG. 1 depicts in cross-section a biomass digester containment structure, according to the invention.

In FIG. 1 a depression 1 in the earth 2 has been formed within an encircling berm 3. The surface of the depression 1 is lined with a lower sealing layer 4 which may be flexible plastic sheet 4 made from vinyl, polyethelene or a similarly compatible material. In a more complex embodiment the surface of the depression 1 may be sealed by cement or some other sealing product.

In a central region of the depression 1 a drainage pipe 5 is installed below the lower sealing layer 4. This pipe 5 communicates through a lower sealed coupling 6 to a network of fluid-extraction tubing 7, located on the other side of the sealing layer 4, that constitutes a collection system. This tubing 7, shown most clearly in FIG. 3, may conveniently be made of perforated plastic tubing that is suitable for the collection of liquids. This tubing 7 would normally rest along the bottom of the biomass 8 directly on the lower layer 4. This tubing 7 is shown in the Figures as being slightly above the layer 4, but this is merely for diagrammatic convenience.

Figure 3:
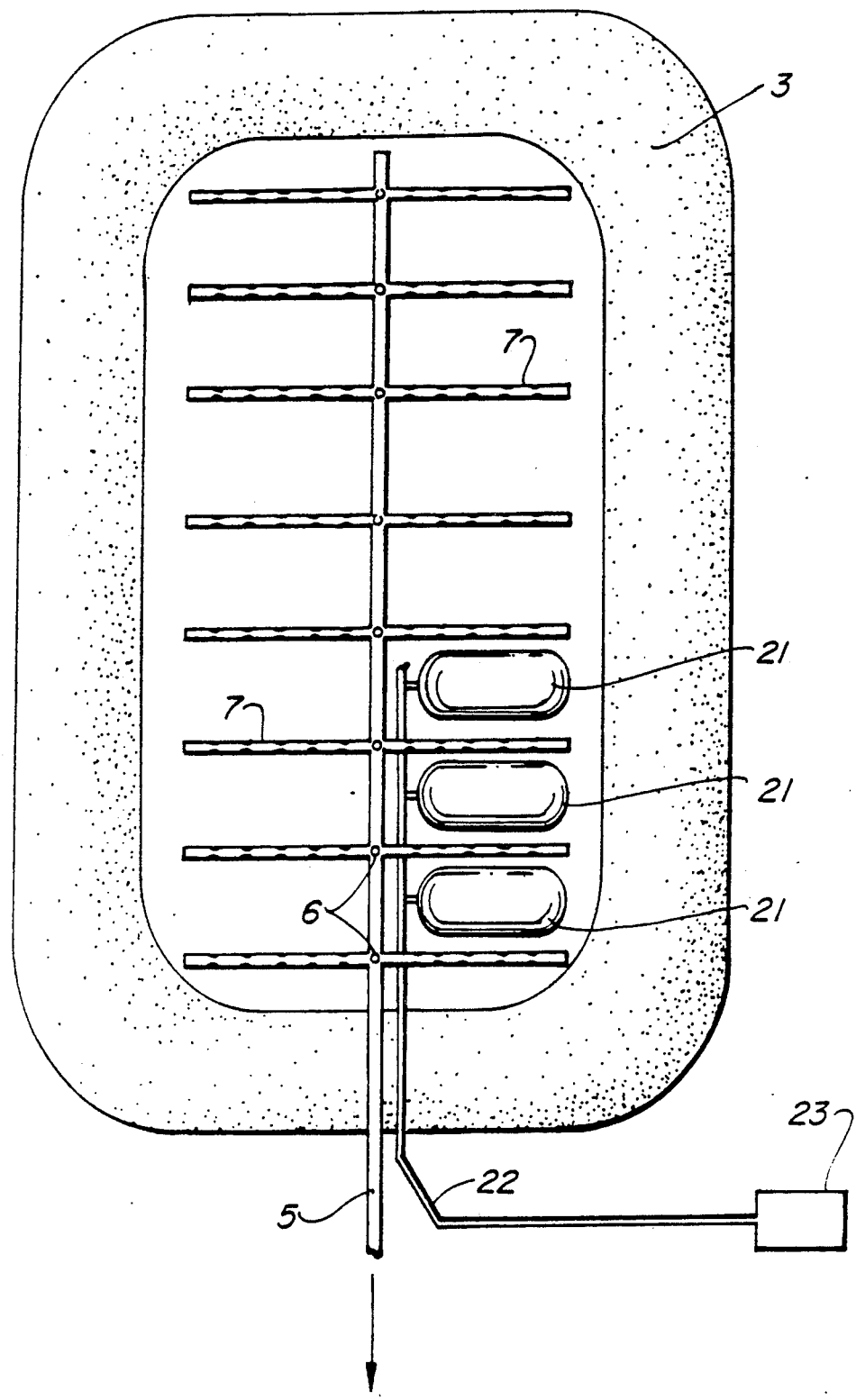
FIG. 3 shows an overhead view of the collection system within the container of FIG. 1.

FIG. 3 shows an overhead view of the collection system within the container of FIG. 1.

Between the tubing 7 may be installed on the floor of the depression 1, above the sealing layer 4, inflatable bladders 21. Only three such bladders are shown in FIG. 3 for simplicity. In use, bladders 21 would be placed between all of the tubes 7. In one alternative, where the lower sealing layer 4 is a flexible sheet, the bladder 21 may be formed by bonding an upper flexible sheet to lower layer 4.

The array of bladders 21 are connected through their own piping network 22 to an external source 23 of gas or fluid that can be used to fill the bladders and create pulsations therein. When it is desired to agitate the biomass 8 the bladders 21 may be inflated and deflated repeatedly.

When the bladders 21 are proximate, and preferably bonded or fastened to the lower layer 4, their inflation will tend to direct fluids, flowing under gravity, to the fluid extraction tubing 7.

Returning to FIG. 1, once the lower containment structure is complete biomass 8 is then deposited within the depression 1. The invention works best with fibrous cellulostic biomass that is readily compressible. Examples are straw and bagass. A network of pipes 9 constituting the reagent distribution system 10 is then laid over the biomass 8. A central header 11 provides an inlet to the distribution system 10 and communicates with the exterior region through sealed connectors (not shown) passing through the upper cover 12 in a manner that will preserve an air tight seal.

Over the distribution system 10 and biomass 8 is placed a collapsible upper cover 12 which may again be made of vinyl or polyethelene sheeting, or a similar suitable material. This upper cover 12 may also be a ridged panel, provided that it has flexible sides that may be sealed to the lower sealing layer 4 in a manner akin to that to be described for sheeting, or other means that allow its vertical movement while maintaining the airtightness of the containment structure.

The sides of the upper cover 12 extend completely over the biomass and down to the border 12 of the lower sealing layer 4 where an air tight seal may be effected.

Figure 4:
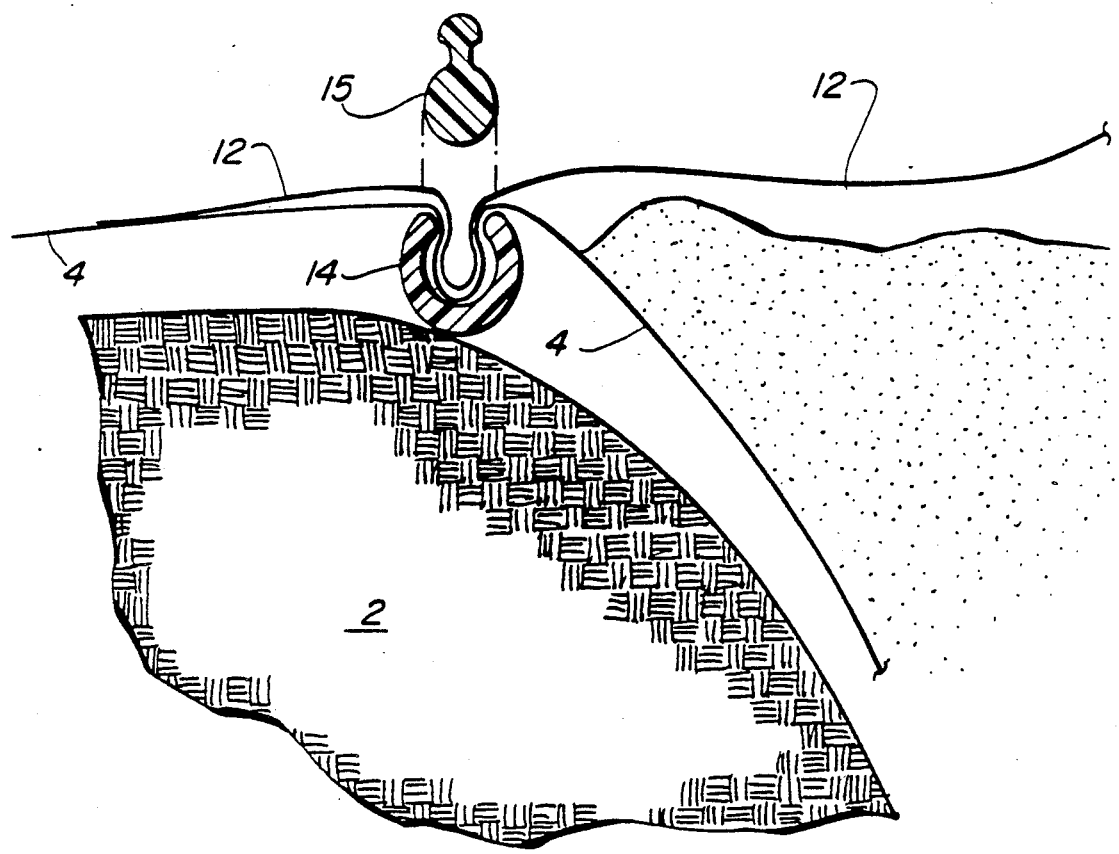
FIG. 4 shows the air tight connection between the upper and lower sheets that contain the biomass.

FIG. 4 shows an enlarged view of one means by which the upper cover 12 may be attached to the lower sealing layer 4, in the case where the lower sealing layer 4 is composed of flexible sheeting.

On the surface of the berm 3 a "C" cross-section sealing strip 14 of flexible material, suitably of extruded plastic, is laid around the entire quantity of biomass. The lower sealing layer 4, in this case a plastic sheet, is laid over the sealing strip 14 so that it may be pressed into the "C" shaped channel. The upper cover 12 is then laid over the same sealing strip 14 and a linear plug 15 inserted snugly within the channel of the sealing strip 14 which is sprung to close in a clamping fashion. This arrangement will provide a sufficient seal to allow an adequate vacuum to be drawn.

Figure 2:
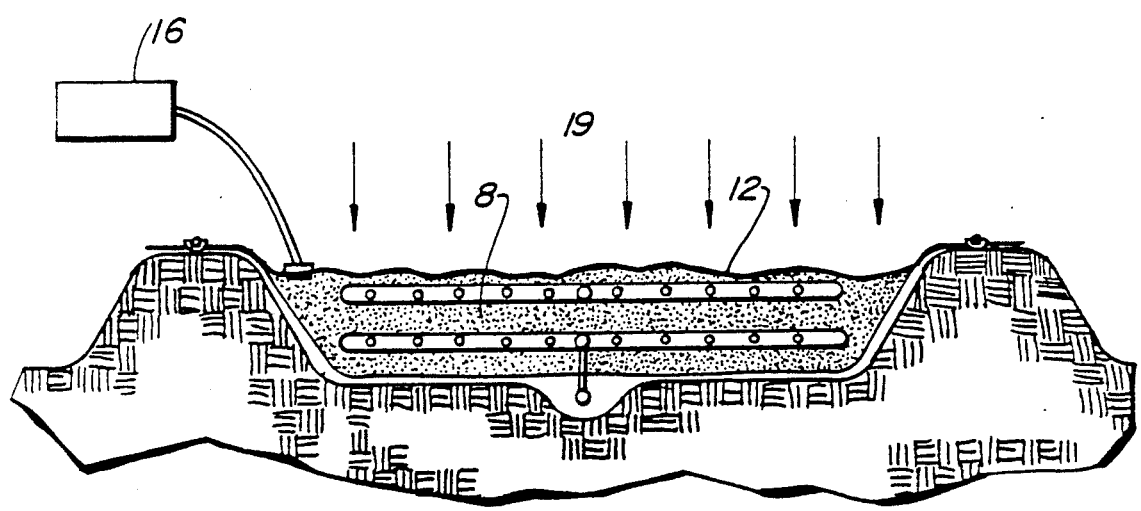
FIG. 2 shows the containment structure of FIG. 1 with a vacuum being drawn.
Figure 5:
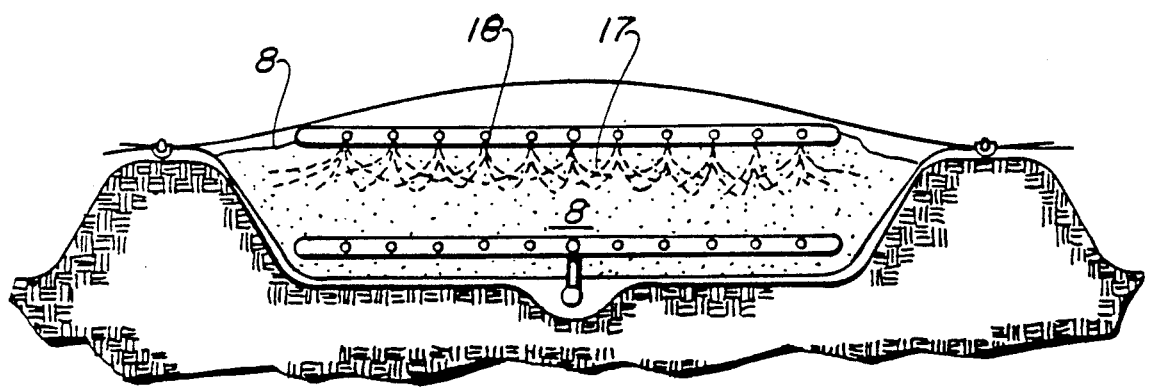
FIG. 5 shows the biomass containment system in the course of depositing a limited quantity of reagent onto a localized upper layer.
Figure 6:
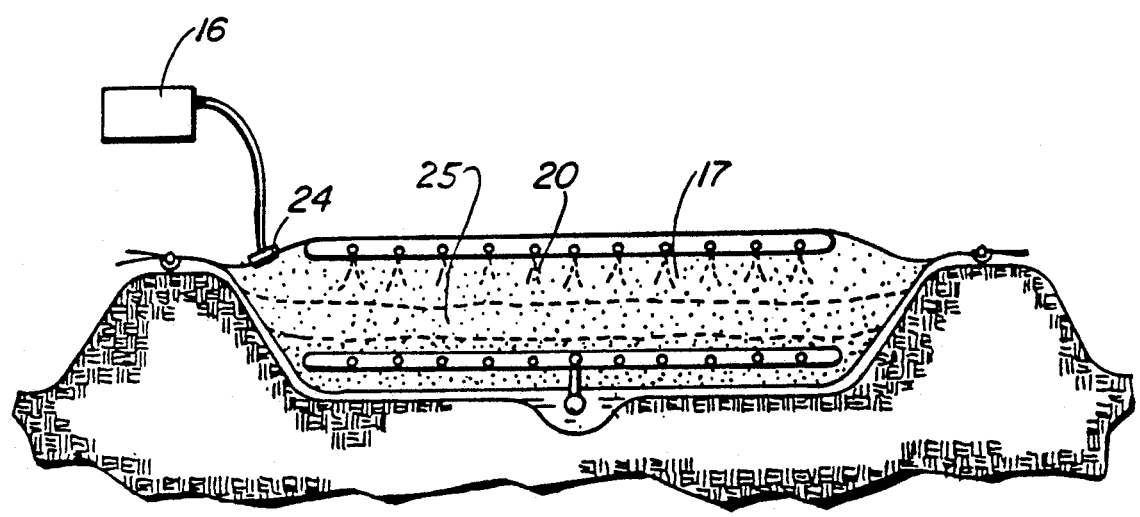
FIG. 6 shows the progressive displacement downwards of an active reagent-containing zone under the influence of vacuum-induced compaction.

A vacuum may be created by use of the standard vacuum pump 16, or any equivalent device for creating a reduced air pressure within the containment structure, shown schematically in FIGS. 1, 2 and 6. This pump may draw air through a hose 17a which communicates with the region under the upper cover 12 through a sealed coupling 24. Once the vacuum pump 16 is activated, the atmospheric pressure arising from the difference created by the reduced internal gas pressure shown by arrows 19 in FIGS. 3 and 5, will apply a compressive force to the upper cover 12. This will cause a collapse and compression of the biomass 8.

Although a "vacuum" is referred to this does not refer to a "perfect" or "high" vacuum. Rather, this word is intended to refer to a condition of reduced pressure sufficient to effect a compression of the biomass matrix.

The ability to effect a compression of the biomass is useful in these respects. If a measured quantity of reagent has been added to the biomass 8 through the distribution system 10, the biomass 8 may be compressed under vacuum to assist in the thorough wetting thereof. If the biomass has been through the digestion process the liquid products may be expressed from the biomass by this compression and withdrawn by the collection system tubing 7 after the liquids have accumulated at the bottom of the biomass 8 under gravity. Water may further be applied, as if it were a reagent, to flush out residual reagent for subsequent separation and recovery. Again, the vacuum compression procedure can enhance the extraction of this rinse water.

When it is desired to remove fluids via the collection system tubing 7, the bladders 21 may be inflated fully to create sloping surfaces that will direct fluids under gravity to that tubing 7. In such application, bladders 21 that are bonded integrally to the lower layer 4 will provide superior performance.

The digestion process may be initiated before drawing a vacuum, by introducing the reagent through the distribution system 10. Sufficient reagent may be added to wet the entire amount of biomass after compression. Alternately only sufficient reagent may be introduced to wet just an upper zone. This depicted in FIG. 5.

In FIG. 5 reagent 18 is being deposited in the upper layer 17 of the biomass 8. Once this layer is wetted the digestion reaction is allowed to proceed to relative completion within the upper layer 17.

A highly concentrated form of reagent 18 may be applied at this stage, allowing that only a reduced quantity is needed to wet the limited volume of the upper layer. This will result in an increase in the rate of the reaction occurring in the upper layer.

Then a displacing or diffusing fluid 20 is distributed over the upper layer 17 by the distribution system. This is shown in FIG. 6. By choosing a displacing fluid 20 that does not impair the performance of the reagent, the presence of this fluid will serve to displace the reagent downward into a lower layer. Alternately, if the displacing fluid 20 dilutes the reagent, such as where water is used, then by using a highly concentrated initial deposit of reagent, the diluted reagent will still retain an adequate degree of reactivity. Thus this second flushing will serve to diffuse the reagent further within the biomass.

The former upper layer 17 will then become occupied by displacing fluid or reagent and displacing fluid combined, and the displacing fluid 20 and the reagent 18 will be carried into a lower zone 25. This process can be enhanced by compressing the biomass 8 under vacuum.

The new zone 25 of reagent 18 may then be allowed to react with the biomass 8 until it is digested. Then further displacing fluid 20 may be applied so as to move the reagent 18 downward to an even lower zone.

The advantage of this process is that less quantity of reagent may be required in order to process the initial quantity of biomass. If the initial application is of a concentrated form of reagent, the reaction will then proceed much faster. Thus, through use of this expanding zone reaction system, the length of time necessary for the entire quantity of biomass to be digested will be reduced.

In operation the sealed containment of the biomass effected by the invention allows the biomass to be held in isolation from exterior contamination by microbes and yeasts. Where it is decided to store biomass in a condition where it will not deteriorate by rotting, an acid reagent e.g. 3.0 pH, may be applied. This will preserve the biomass in a "pickled condition".

Sodium hydroxide is an inexpensive reagent suitable for this application that may be used at concentrations of 1% in aqueous solution. Potassium hydroxide may also be used at 0.25% solution. Further, sterilizing gases such as ammonia may also be introduced through the fluid distribution system.

When it is desired to reactivate the digestion process, the acid may be flushed-out by applying a large quantity of water, or may be neutralized by applying a basic solution.

Once the biomass is sterilized, it may be inoculated with a preferred fungus and yeasts adapted to consume cellulose or hemi-cellulose and produce sugars, glucose and ultimately proteins. Examples of such Fungi are *Trichoderma Viride* and *Asperqillus Niger*. The action of such bioreactants will convert a portion of the useless cellulose in the biomass to valuable protein, suitable for animal feed.

Once the cellulose and hemi-celluose has been sufficiently denatured by the action of the Fungi and yeasts, enzymes may build-up that are deleterious to further fermentation. Using the fluid distribution and collection system, combined with vacuum agitation, the biomass may be flushed with water or other appropriate liquids to remove such products. The action of vacuum compaction and release, enhanced by the inflation of the floor-mounted bladders, will agitate the biomass and enhance the flushing process. In this manner, feedback inhibition may be overcome.

The presence of reagent distribution 10 and collection systems 7 within the enclosure for the biomass 8 has further particular utility. Heat generated within the biomass 8 may be removed by extracting liquids that carry the heat with them, cooling the liquids externally, and then re-injecting the liquids through the distribution system 10 where required to maintain the digestion process or to further cool the biomass.

The application of vacuum compression to the biomass 8 will facilitate this cooling cycle by speeding the expression of heat-removing liquids from the biomass.

The ability to recycle digestion fluids through the biomass after extraction can also serve to partially filter-out organisms suspended in such liquids. Again, vacuum compression may be applied so as to compact the fibrous mass of biomass within the digester. In this compacted condition the digestion liquid may be repeatedly removed through the bottom collection system 7, filtered, and reapplied from above through the upper distribution system 10 where it may then percolate downwards under gravity. This repeated cycling of the liquid through the compacted biomass will serve to partially filter-out yeast organisms and prevent over population inhibitions.

The foregoing disclosure constitutes a description of several preferred embodiments of the invention. The invention in its broadest and more particular aspects is more precisely defined in the claims which follow.

I claim:

1. A containment structure for use in compacting and treating a matrix of fibrous, compressible biomass comprising:
   (a) a compressible, enveloping, air-tight enclosure having a downwardly displaceable upper cover overlying a matrix of fibrous, compressible biomass placed therein,
   (b) a vacuum pump communicating with the biomass in said containment structure through a conduit adapted to evacuate gas from the matrix of biomass within the containment structure and thereby cause the upper cover, by displacement, to compact said biomass,
   (c) reagent means for chemically digesting said biomass, and
   (d) reagent-distribution and fluid collection systems respectively installed in the upper and lower regions of the containment structures above and below and in communication with the biomass placed within said containment structure,
   to thereby provide a means by which said biomass may be treated by vacuum compaction and agitation, in conjunction with the distribution of reagents within the biomass through the upper reagent distribution system, and the collection through the lower collection system of fluid products that have percolated through the biomass.

2. A containment structure as in claim 1 wherein the upper cover of said containment structure comprises a flexible sheet which forms the upper surface of said structure.

3. A containment structure as in claim 1 wherein the central portion of the cover is solid and the outside border of said upper cover is comprised of flexible sheet material.

4. A containment structure for use in compacting and treating a matrix of fibrous, compressible biomass comprising:
   (1) a compressible, enveloping, air-tight enclosure having an upper cover, a lower surface constituting a floor, and a matrix of fibrous, compressible biomass placed therein,
   (2) a vacuum pump communicating with said containment structure through a conduit adapted to evacuate gas from the containment structure and thereby compact said biomass, and
   (3) reagent-distribution and fluid collection systems respectively installed in the upper and lower regions of the containment structures above and below the biomass placed within said containment structure,
wherein said fluid collection system comprises a series of spaced collection tubes located along the floor of said structure, and said containment structure further comprises:
   (a) a series of inflatable bladders located along the floor of said structure in spaces between said collection tubes, said bladders being adapted to agitate said biomass upon inflation and deflation, and further being adapted on inflation to direct fluid falling within the containment structure under the influence of gravity towards said collection tubes, and
   (b) a means to inflate and deflate said bladders located exterior to and connected to said containment structure.

5. A containment structure as in claim 4 wherein said bladders are each comprised of an upper flexible sheet which is integrally attached around its outer edges to the lower surface of the containment structure.

* * * * *